(12) United States Patent
Batzinger et al.

(10) Patent No.: US 8,181,523 B2
(45) Date of Patent: May 22, 2012

(54) ULTRASOUND INSPECTION METHODS FOR NOISY CAST MATERIALS AND RELATED PROBES

(75) Inventors: Thomas James Batzinger, Burnt Hills, NY (US); Riccardo Barigazzi, Florence (IT); Fabrizio Betti, Florence (IT); Waseem Ibrahim Faidi, Schenectady, NY (US); Eugenio Giorni, Florence (IT); Dane E. Hackenberger, Mifflintown, PA (US); Federico Iozzelli, Pistoia (IT); Manoj Kumar Km, Bangalore (IN); Zongqi Sun, Albany, NY (US); Toby L. Sweigart, Burnham, PA (US)

(73) Assignee: Nuovo Pignone S.p.A., Florence (IT)

( * ) Notice: Subject to any disclaimer, the term of this patent is extended or adjusted under 35 U.S.C. 154(b) by 657 days.

(21) Appl. No.: 12/338,495

(22) Filed: Dec. 18, 2008

(65) Prior Publication Data
US 2010/0018311 A1    Jan. 28, 2010

Related U.S. Application Data

(66) Substitute for application No. 61/082,669, filed on Jul. 22, 2008.

(51) Int. Cl.
*G01N 29/12* (2006.01)
(52) U.S. Cl. ............................ 73/579; 73/598; 73/644
(58) Field of Classification Search .................... 73/579, 73/597, 598, 587, 599, 602, 614, 620, 622, 73/644
See application file for complete search history.

(56) References Cited

U.S. PATENT DOCUMENTS

| | | | |
|---|---|---|---|
| 5,635,644 A * | 6/1997 | Ishikawa et al. | 73/614 |
| 6,164,136 A * | 12/2000 | Hirsekorn et al. | 73/602 |
| 7,293,461 B1 * | 11/2007 | Girndt | 73/622 |
| 7,696,672 B2 * | 4/2010 | Sugiura et al. | 310/334 |
| 7,808,156 B2 * | 10/2010 | Chaggares et al. | 310/334 |
| 2011/0057545 A1 * | 3/2011 | Chaggares et al. | 310/334 |

FOREIGN PATENT DOCUMENTS
FR    2475836    * 8/1981
* cited by examiner

*Primary Examiner* — J M Saint Surin
(74) *Attorney, Agent, or Firm* — Potomac Patent Group PLLC

(57) ABSTRACT

Ultrasound inspection methods for noisy materials and related probes are disclosed to inspect a defect in a cast material that use polycarbonate delay layers having a first surface configured to be disposed on a surface of the cast material; and an acoustic crystal element disposed on a second surface of the polycarbonate delay layer.

21 Claims, 6 Drawing Sheets

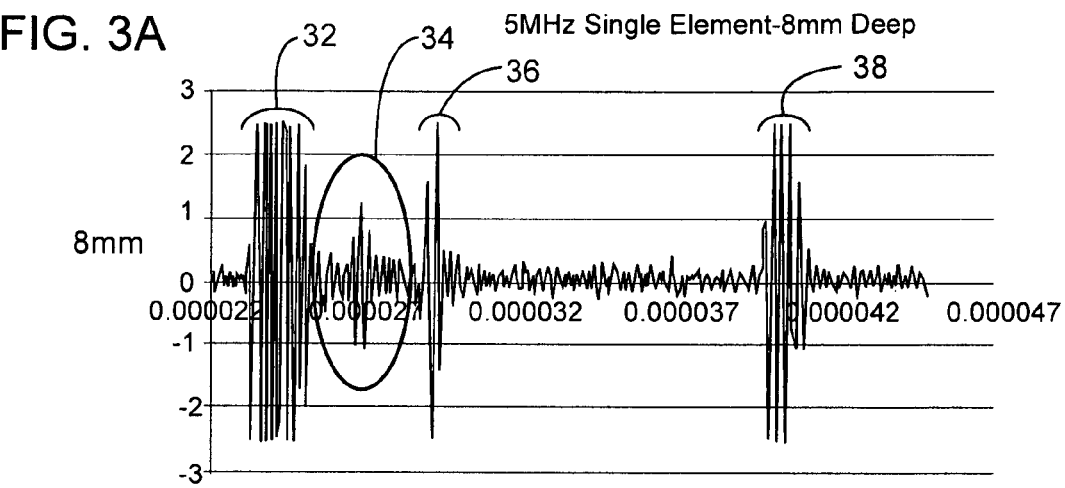
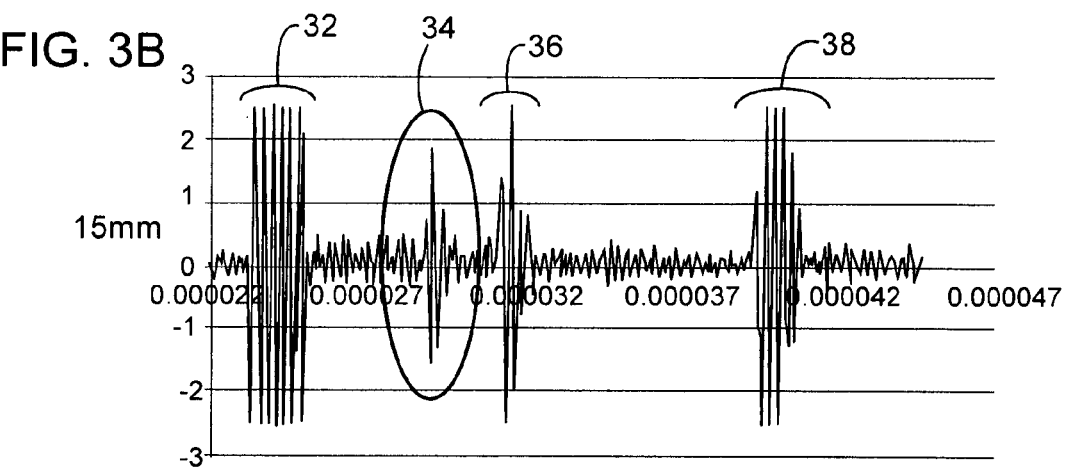
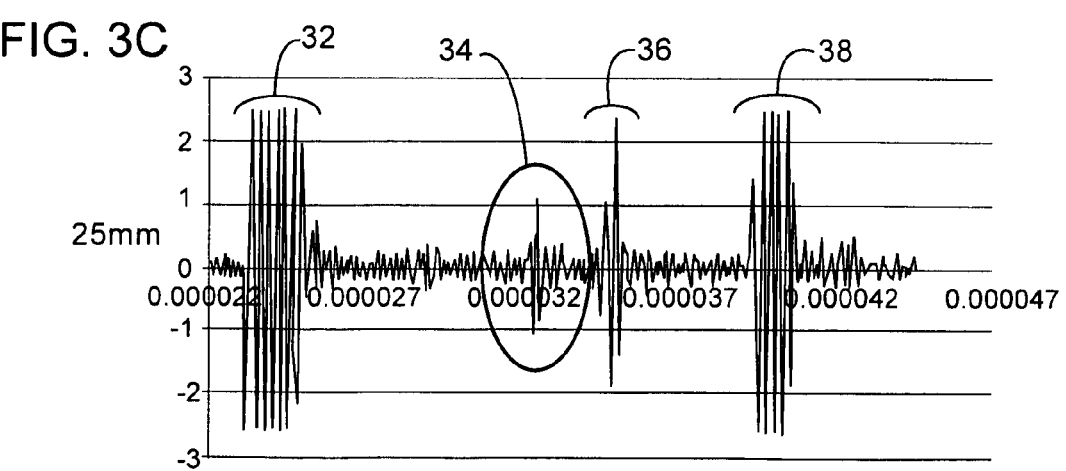

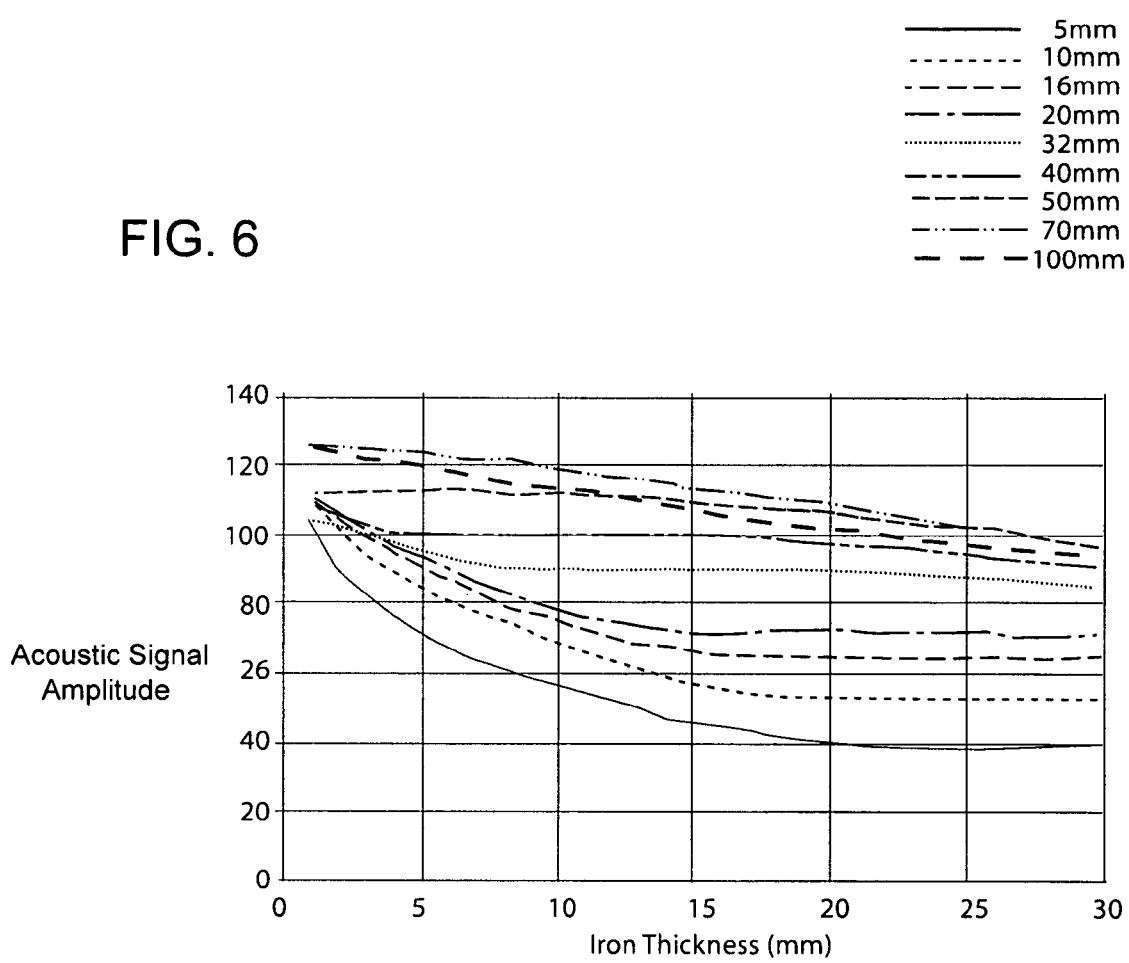

ULTRASOUND INSPECTION METHODS FOR NOISY CAST MATERIALS AND RELATED PROBES

CROSS REFERENCE TO RELATED APPLICATIONS

This application is related to, and claims priority from, U.S. Provisional Patent Application of Ser. No. 61/082,669, filed on Jul. 22, 2008, the contents of which are herein incorporated by reference in their entirety.

BACKGROUND OF THE INVENTION

1. Field of the Invention

The embodiments disclosed relate generally to non-destructive testing and more particularly to ultrasound inspection methods for noisy materials and related probes.

2. Description of the Related Art

Casting is widely used in many industrial applications to manufacture intricate and expensive parts. As understood by those of ordinary skill in the applicable arts, castings are manufactured in rough forms and further machined into final shapes, which in many applications require high-quality sealing surfaces obtained through detailed final machining cuts. However, inherent to casting processes are shrinkage, inclusions, or voids in the cast part created at least in part by dirt or sand coming off from the mold or material shrinkage during solidification. As such, when rough cast parts are machined into final products, many times subsurface areas of shrinkage, inclusions, or voids are reached, generating a defect that, at a minimum, has to be repaired, or, at a worst case scenario, requires that part must be scrapped.

In the Oil and Gas industry, for example, casting is used for the production of large industrial component manufactured for use in oil and gas production and transmission systems. There are generally three cast materials used for these components—nodular cast iron, flake cast iron, and cast steel. Depending on the type of cast material used and the location of the defects discovered, the cast materials may be repaired or may be scrapped for remelting, thus contributing to an increase in manufacturing cost due to either the repair cost and/or lead-time required to replace scrapped castings.

X-ray, eddy current inspection, magnetic particle inspection, liquid dye penetrant, and ultrasound are various examples of commonly used techniques to inspect cast materials. However, these conventional techniques are limited in their ability to detect small subsurface defects. In liquid-dye-penetrant techniques, a die is spread over a surface to be inspected and excess dye material is wiped off, leaving only that portion of the dye that was absorbed in a defect. A powder absorbing material is then used to locate the surface defect. Similarly, in magnetic-particle inspection, magnetic particles are spread over the surface to be tested and a magnetic field is applied, causing the particles to concentrate in an area where the magnetic field leaks are caused by the defect. In view of their very nature, neither liquid-dye-penetrant nor magnetic-particle inspection techniques can be used to detect small subsurface defects in cast parts.

In eddy-current inspection, circulating (or eddy) currents generated at the surface and near surface of a part being inspected are perturbed by defects and detected by the eddy-current inspection system. However, as understood by those of ordinary skill, small defects are difficult to detect deep below the inspection surface with eddy currents because the skin effects quickly attenuate the energy getting into the surface and because the effective area increases with depth, thus increasing the size of the smallest defect that can be detected. X-ray techniques use a radiation source that penetrates through the thickness of the test piece to record defects on a X-ray detector placed opposite to the radiation source. However, the size of defects detected by X-ray inspection is limited to about 2% of the thickness of the sample, which thickness may range from 50 mm to over 300 mm thick. Thus, the ability to inspect thick parts with X-ray devices is significantly reduced. In addition, specialized high-energy X-ray facilities or gamma ray instrumentation are required for these types of inspection, thus limiting the number of casting suppliers that are capable to invest in expensive facilities to conduct high-energy, X-ray or gamma-ray inspection of large castings.

Ultrasonic inspection has been used for cast material inspection for many years. It is commonly considered that the resolution of defects when using ultrasound in cast materials is limited due to the nature of the microstructure of cast materials. Nodular cast iron and flake cast iron contain a great deal of carbon segregated from the iron. The segregated carbon in these materials will scatter the ultrasound leading to very noisy ultrasonic signals. One of the challenges to inspecting casting materials using ultrasound is to be able to discriminate defect signals from normal cast material microstructure scatter signals. However, conventional scattering theory teaches that the frequency of the acoustic energy should be decreased for the detection of defects in cast materials in thicker parts. Conventionally, dual element probes operating at frequencies between 1 MHz and 5 MHz are used to reduce the sensitivity to scatter and retain sensitivity to the defects, but their performance to detect defects having a characteristic length of about 0.5 mm is not satisfactory.

It would therefore be desirable to develop new ultrasound inspection methods and related probes for noisy materials with increased sensitivity to small subsurface defects, while maintaining or reducing the sensitivity to microstructure background noise.

BRIEF SUMMARY OF THE INVENTION

One or more of the above-summarized needs or others known in the art are addressed by utilizing a polycarbonate delay layer bonded to a single element ultrasonic probe.

This polycarbonate delay layer bonded to a single element ultrasonic probe reduces sensitivity to background noise from a microstructure of the cast material and increases sensitivity to a scatter acoustic signal from the defect.

Methods of detecting a defect in a noisy material are also within the scope of the subject matter disclosed herein. Such methods include steps of emitting an amount of acoustic energy from an acoustic crystal element through a polycarbonate delay layer attached to the acoustic crystal element; and detecting the defect in the noisy material based on a measurement of a portion of the emitted acoustic energy scattered by the defect through the polycarbonate delay.

The above brief description sets forth features of the various embodiments of the present invention in order that the detailed description that follows may be better understood, and in order that the present contributions to the art may be better appreciated. There are, of course, other features of the invention that will be described hereinafter and which will be for the subject matter of the appended claims.

In this respect, before explaining several embodiments of the invention in detail, it is understood that the various embodiments of the invention are not limited in their application to the details of the construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which the disclosure is based, may readily be utilized as a basis for designing other structures, methods, and/or systems for carrying out the several purposes of the present invention. It is important, therefore, that the claims be regarded as including such equivalent constructions insofar as they do not depart from the spirit and scope of the present invention.

Further, the purpose of the foregoing Abstract is to enable a patent examiner and/or the public generally, and especially scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

BRIEF DESCRIPTION OF THE DRAWINGS

A more complete appreciation of the disclosed embodiments of the invention and many of the attendant advantages thereof will be readily obtained as the same becomes better understood by reference to the following detailed description when considered in connection with the accompanying drawings, wherein:

FIG. 3A-3C illustrate variations of measured signal as a function of time for the single-element ultrasound inspection probe for defects at exemplary depths of 8, 15, and 25 mm, respectively, for a calibration standard block of nodular cast iron;

FIG. 6 illustrates simulation results on the variation of acoustic signal amplitude in arbitrary units as a function of iron thickness depth for delay layers varying in thickness from 5 to 100 mm for a single-element acoustic inspection probe;

DETAILED DESCRIPTION OF THE PREFERRED EMBODIMENTS

Figure 1:
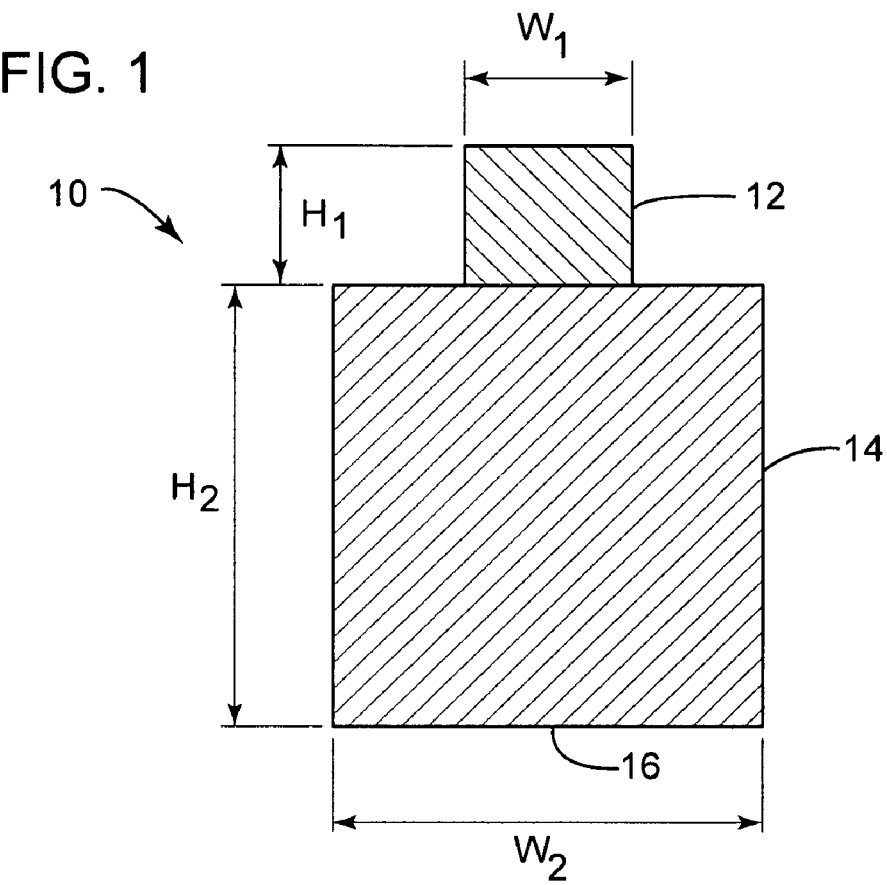
FIG. 1 illustrates a schematic of a single-element ultrasound inspection probe according to an embodiment of the subject matter disclosed.

Embodiments of the subject matter disclosed relate generally to non-destructive testing and more particularly to ultrasound probes and related methods for inspection of cast materials. The use of a polycarbonate delay in the disclosed single-element ultrasound inspection probes has for the first time allowed detection of subsurface casting defects in nodular and flake cast iron parts with characteristic dimensions as small as 0.5 mm or 3.0 mm, respectively, never before measured using ultrasound detection techniques at frequencies heretofore believed too high, thus generating microstructure background scattering with unacceptable signal-to-noise ratios.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Referring now to the drawings, wherein like reference numerals designate identical or corresponding parts throughout the several views, embodiments of the improved ultrasound inspection probes will be described.

FIG. 1 illustrates a schematic diagram of a single-element ultrasound inspection probe 10 according to one embodiment of the subject matter disclosed herein. As shown, the single-element ultrasound inspection probe 10 includes a contact ultrasound transducer (having an ultrasound generating element with appropriate electrical connection, a matching layer (not shown), and a backing layer (not shown), hereinafter collectively referred to as ultrasound transducer or crystal element 12) mounted on top of a polycarbonate delay 14. The contact element 12 has a characteristic dimension $L_1$, which may be a diameter if the contact element 12 is cylindrical. Also, as shown in FIG. 1, the polycarbonate delay 14 has a height $H_2$ and a width $W_2$, which may also be a diameter for embodiments having a cylindrical polycarbonate delay 14. In use, a lower surface 16 of the polycarbonate delay 14 is mounted to a surface to be inspected and the contact element 12 is driven at the appropriate frequency to generate a beam of acoustic energy into the surface. Selection of a frequency to drive the contact element 12, diameter of the contact element 12, and dimensional characteristics of the polycarbonate delay 14 produces the desired beam of acoustic energy for the single-element ultrasound inspection probe 10. As understood by those of ordinary skill, the contact element 12 also servers as a receiver of acoustic energy scattered from the casting that is further processed in order to detect defects in the part being inspected.

As it will become more apparent from the subject matter disclosed herein, ranges of the above-noted parameters of the single-element ultrasound inspection probe 10 are contemplated for the various possible embodiments thereof in order to allow for the inspection of noisy materials. This includes the type of the transducer active element (its geometry and operating frequency), electrical connections, a matching layer, and a backing layer. As it is apparent to those of ordinary skill of the art, the ultrasound element may also be a linear or phased array in one-dimensional or two-dimensional arrangement. As used herein throughout, the expression noisy materials means materials in which the nature of their microstructure will scatter the ultrasound energy, which precludes the detection of small defects. The expression noisy material is not intended to be limited to a cast material. As those of ordinary skill in the art will appreciate, after review of the disclosed subject matter, embodiments of the disclosed inventions may be applied to other materials with structures that reflect and/or scatter the ultrasound energy generating noise in the received signal and rendering smaller defects difficult to detect. Examples of such materials include, but are not limited to, composite materials, ceramic, and structurally porous material in addition to nodular cast iron, flake cast iron, and cast steel.

As already noted, cast iron materials are typically difficult to inspect using ultrasound. The single-element ultrasound inspection probe 10 with the polycarbonate delay 14 provides a better signal-to-noise ratio in detecting defects in cast iron materials, such as, but not limited to, flake and nodular cast iron. The polycarbonate delay 14 produces better ultrasonic beam properties required for increased inspection performance. One of the advantageous features of the single-element ultrasound inspection probe 10 includes its design with the selection of the delay to maximize the sensitivity to defects in cast iron materials while minimizing sensitivity to intrinsic material characteristics such as casting material microstructure features, as it will be further explained below.

In the illustration shown in FIG. 1, the contact element 12 is a 5-MHz transducer having a circular cross section of about 12.7 mm (about 0.5 in) in diameter and the polycarbonate layer 14 is in the shape of a cylinder with a height, $H_2$, of approximately 32 mm (about 1.25 in) and a diameter, $L_2$, of approximately 38 mm (about 1.5 in); however, other shapes and sizes may be used within the scope of the subject matter disclosed. For example, but not to be considered as a limitation, the polycarbonate layer 14 may have a rectangular or square cross section. In addition, as those of ordinary skill in the applicable arts will appreciate after reviewing the subject matter disclosed herein, the shape of the polycarbonate layer 14 is not limiting as long as its lateral area is large enough so that ultrasound waves do not interfere with its sidewall.

As it will become more apparent below, extensive experimental measurements and numerical modeling have allowed the development of an engineered shape and height of the polycarbonate delay 14 that, together with the selection of the driving frequency of the contact element 12, allowed the inventors to reach desired levels of SNR as further demonstrated below in the summary of experiments and modeling results. It is believed that the polycarbonate delay 14 acts like a filter for some of the scattered acoustic energy from the microstructure of the casting parts being inspected, but signal from the defects are more direct and are then detected by the sensor preferentially compared to the background noise from the microstructure. It is further believed that the acoustic scattered signals from the microstructure come off at various angles that are scattered away from the reception portion of the probe at the polycarbonate delay 14 and scatter from the defect is more direct, reaches the sensor element 12, and is detected.

It should be noted herein that conventional scattering theory teaches that in acoustic sensors used to detect defects in casting parts one should decrease the frequency in order to reach deeper into the part. As it will be shown, these inventors have actually increased the frequency to increase sensitivity to small defects while the polycarbonate delay 14 allows sensitivity to the scatter from the defect and attenuation of scatter from the microstructure. Normally, a SNR of three-to-one is desired. Exemplary embodiments of the polycarbonate delay 14 include, but are not limited to, Lucite and Rexolite. One of the advantageous feature of the single-element ultrasound inspection probe 10 is the fact that ultrasonic inspection may potentially find defects before the manufacturing while cast materials are still at the foundries, thereby allowing for the part to be repaired or rejected and thus avoiding significant and unnecessary manufacturing costs.

Conventionally when inspecting noisy cast materials dual-element probes have been used. In order to evaluate the performance of an embodiment of the single-element ultrasound inspection probe 10 in noisy materials, calibration standards were manufactured of nodular cast iron, flake cast iron, and cast steel and measurements of these standards were made and compared using an embodiment of the single-element ultrasound inspection probe 10 and two conventional dual-element ultrasound inspection probes. The first conventional dual-element probe was a 2.25-MHz probe, hereinafter Conventional Probe A, and a second conventional dual-element probe was a 5-MHz dual-element probe, hereinafter Conventional Probe B. However, as already noted, the subject matter disclosed herein is equally applicable to other materials, including, but not being limited to, composite materials, ceramic, and structurally porous material.

Figure 2:
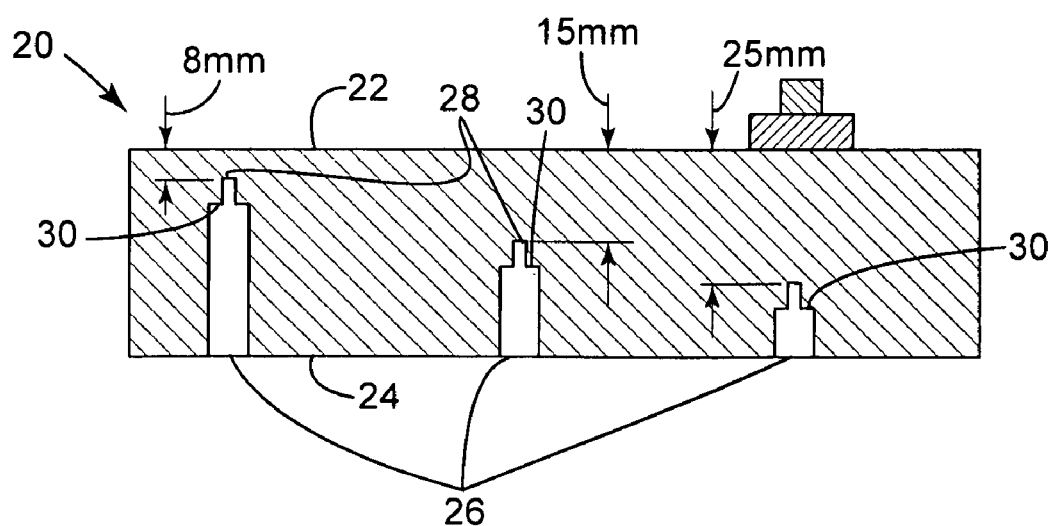
FIG. 2 illustrates a non-destructive evaluation calibration standard used in performance comparisons of single-element ultrasound inspection probes according to embodiments of the subject matter disclosed and conventional probes.

FIG. 2 illustrates an exemplary embodiment of one of the calibration standards having simulated defects at three different depths (8, 15, and 25 mm). These standards were blocks 20 having a front surface 22, a bottom surface 24, and a set of flat-bottom holes 26 (or FBH) of different sizes (ranging from about 0.5 to 5 mm) and depths (ranging from 0 to about 35 mm) to simulate defects in the various materials. In the exemplary calibration standards of FIG. 2 each flat-bottom hole 26 included a 0.5-mm diameter hole 28 with a counter bore 30. In order to include the effects of the casting surface condition, as-cast and machined blocks 20 were constructed. The machined surfaces were generated with grinding to a surface roughness of 64 micro inches. Additionally, another calibration standard was made of a rolled steel material with a machined surface to be used as the entitlement in the evaluation process.

Each one of the blocks 20 contained a set of steps of certain thicknesses with flat and smooth surfaces so as to generate "back-wall" signals at the given depths. FIG. 3A-3C illustrate variations of signal as a function of time from the single-element ultrasound inspection probe 10 for measurements of the simulated defects at 8, 15, and 25 mm, respectively for a nodular casting calibration standard block 20. As shown, a typical measurement signal included detections of the front surface 22 at the portion of the signal labeled 32, a signal corresponding to the detection of each flat-bottom hole 26 at 34, detection of the counter bore 30 at 36, and detection of the bottom surface 24 at 38. As explained, different depth ranges (0 to 35 mm) and defect diameters (0.5 to 5 mm) were studied with the use of different blocks 20 made of nodular cast iron, flake cast iron, and cast steel. As those of ordinary skill in the art will understand it, the height of the polycarbonate delay 14 of the single-element probes according the various embodiments disclosed might be optimized for a particular range of depths.

Feasibility tests were conducted using both immersion and contact inspection techniques. The immersion technique was considered entitlement (or the best possible performance) for this process while contact scanning would provide a baseline of presently used inspection processes. The blocks 20 containing flat-bottom holes 26 were scanned and the SNR was calculated using standard procedures by comparing the peak amplitude from a defect and the peak signal from the normal microstructure scatter. The goal was to achieve a SNR of 3 or greater from the defects of interest in the cast materials evaluated. Baseline tests conducted demonstrated that presently used contact inspection processes and immersion inspection techniques failed to provide a SNR ratio of 3 or greater on all cast materials. Detection of 0.5-mm diameter artificial defects in a cast steel piece was possible due to the low amplitude of the microstructure scatter relative to the defect signal, while detection in similar defects in a cast iron material presented a more difficult challenge. The graphite nodules and flakes produced microstructural scatter signals with greater amplitude than observed from the cast steel. When tested using immersion inspection techniques, scatter from the graphite in nodular cast iron was observed to be elevated with respect to steel, but not great enough to prohibit the detection of the 0.5-mm diameter flat-bottom holes. When testing the presently used contact methods on nodular cast iron, the SNR for this material prohibited the detection of 0.5-mm diameter flat-bottom holes. For flake cast iron, the microstructure scatter prohibited detection of 0.5-mm flat-bottom hole by all methods. In addition to the effect from the microstructure, the surface roughness also played a role in the degradation of SNR. Considering these effects, a range of values of inspection variables determined to be critical-to-quality was developed, including flat-bottom hole located at depths ranging from 0 to 30 mm and flat-bottom hole diameters in the range of 0 to 3 mm for various finish of nodular cast iron and flake cast iron. It should be noted that although the tests and modeling results disclosed herein have been carried out for nodular and flake cast iron parts, the disclosed probes and methods are applicable for the inspection of other cast materials; thus, the two exemplary test and modeling results should not be considered as limiting in any way.

Tests conducted using the flat-bottom holes 26 in the blocks 20 in nodular cast iron and flake cast iron demonstrated that the Conventional Probes A and B were not capable to overcome the above-noted microstructure scatter effects. The Conventional Probe A provided reasonable reduction of scatter signal, but was not capable of detecting a 0.5-mm-diameter flat-bottom hole with sufficient SNR. An ultrasonic 2-MHz wavelength is approximately 3 to 4 times greater than the defect of interest. This wavelength-to-defect ratio reduces the ability to resolve these defects. As such, a higher ultrasonic frequency would be required to resolve the defects of interest. One concern with using higher inspection frequency is the fact that the scatter from the normal cast material microstructure increases with the frequency of inspection. A frequency best suited to resolve the defects of interest with sufficient SNR had to be determined. As already noted, for reasonable detection of defects in a structure, a SNR of 3 is considered adequate for the differentiation between defects and microstructure scatter.

Figure 4:
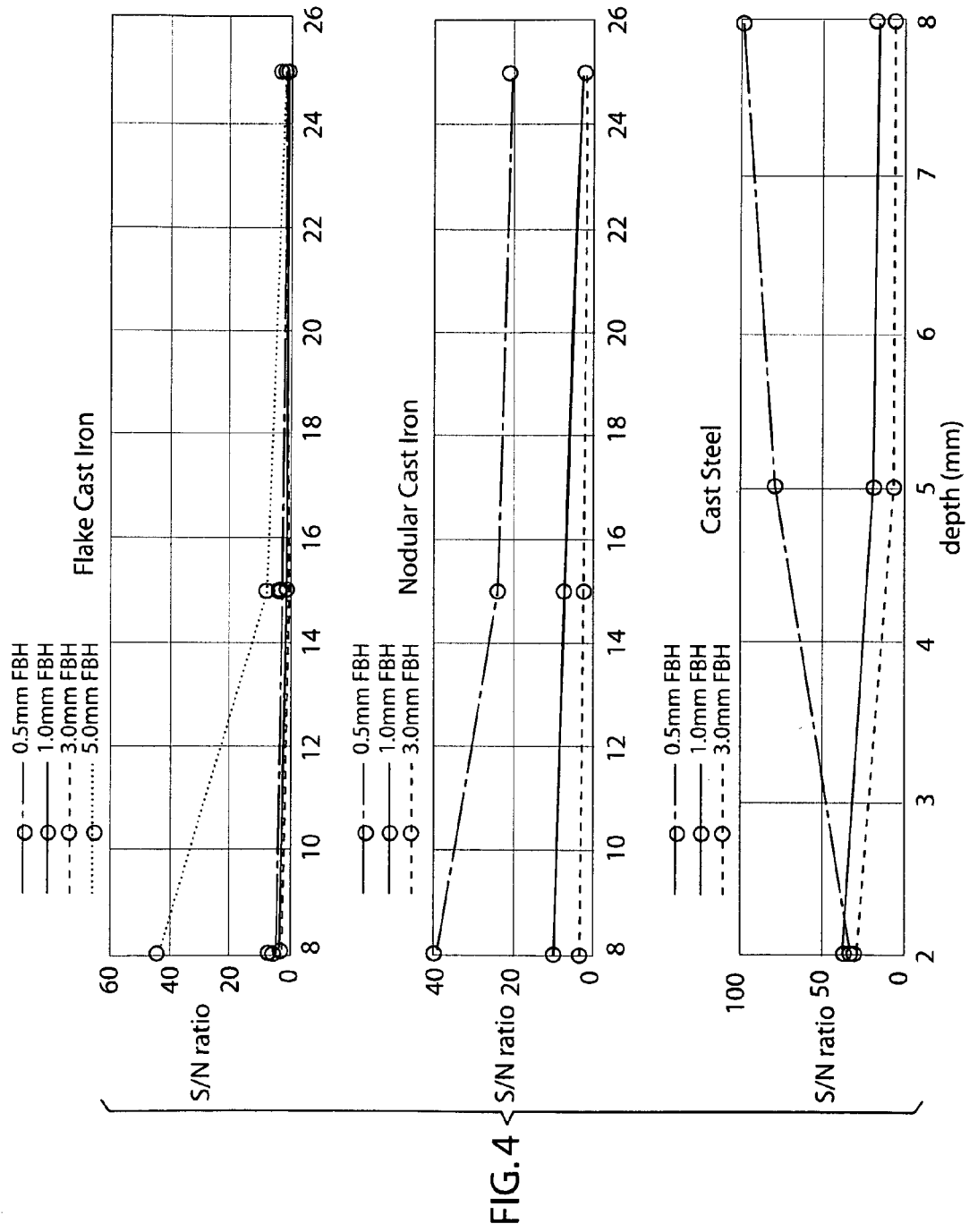
FIG. 4 illustrates the variation of signal-to-noise ration as a function of flat-bottom-hole depth for inspection measurements in various materials using the conventional dual-element probe.
Figure 5:
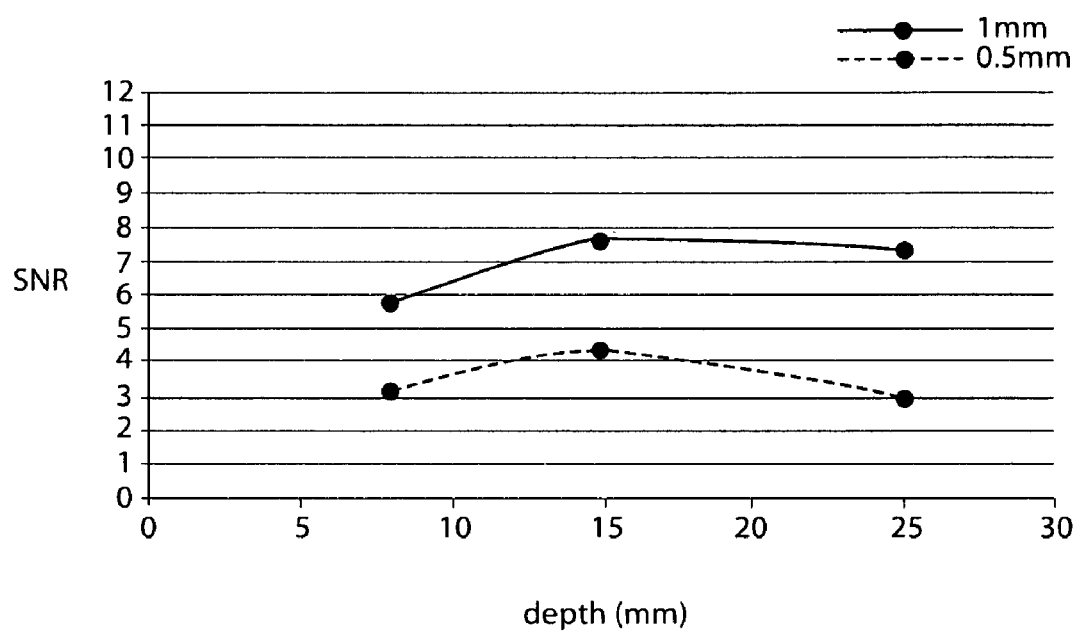
FIG. 5 illustrates the variation of signal-to-noise ratio as a function of flat-bottom hole depth for the single-element ultrasound inspection probe of FIG. 1.

Experimental tests were carried out using the Conventional Probes A and B and an embodiment of the single-element ultrasound inspection probe 10 on sets of flat-bottom holes 26 in different calibration blocks 20 and SNRs were recorded. FIGS. 4 and 5 show the variation of SNR versus flat-bottom-hole depths for three flat-bottom-hole diameters for the Conventional Probes A (FIG. 4) and the single-element ultrasound inspection probe 10 (FIG. 5). The results of these tests showed that the conventional probe B produced greater SNR values in the cast steel block and the 8-mm FBH in the cast iron blocks, while the conventional probe A performed better with the deeper FBH in the cast iron blocks. This was due to the increased frequency-dependent attenuation in cast iron compared to the attenuation in the cast steel. The results in FIG. 5 for the single-element ultrasound inspection probe 10 showed that SNRs were above the acceptance criterion of 3 and varied little with different FBH depths. In summary, for calibration blocks made of nodular cast iron (defects with diameters of 0.5 mm or larger), flake cast iron (defects with diameters of 3 mm or larger), and cast steel (defects with diameters of 0.5 mm or larger), SNRs in measurements made with single-element ultrasound inspection probes according the subject matter disclosed herein in the noted range of depths were all higher than 3, varying, for the noted smallest defect diameters in nodular cast iron, flake cast iron, and cast steel, from 4 to 8.7, from 6.7 to 7.9, and from 3 to 13, respectively.

The optimum operating frequency for the single-element ultrasound inspection probe 10 was found to be between 3 MHz to 5 MHz, with the higher frequencies performing better when the material was changed from flake cast iron to nodular cast iron, and to cast steel (reduction of microstructural noise). Field trials have also been conducted at manufacturing plants of the assignee of this application as well as two plants from manufacturing suppliers. Field trials have been conducted on components cast from all three materials. Ultrasonic indications using various embodiments of the single-element ultrasound inspection probe 10 were detected in all materials tested in the field.

In order to further investigate and optimize probe performance, the behavior of novel and advantageous single-element acoustic inspection probe 10 and the conventional dual-element acoustic probes were modeled through acoustic field calculations carried out by numerical simulations. A dual-element probe with multiple frequencies and a single-element probe with different lengths of delay lines, different delay line materials, delay line thickness, delay line diameter, and operating frequencies were compared by numerical simulations. The model is used to study the response from defects of varying dimensions and at varying depth. All the dimensional parameters associated with the modeled probes are kept constant during the modeling study. Model results for the conventional dual-element probes agreed well with the experimental performance of their counterpart as explained hereinabove.

FIG. 6 shows simulation results on the variation of acoustic signal amplitude as a function of iron depth for delay layers varying in thickness from 5 to 100 mm. In this particular results, the delay layer material simulated was Lucite. As shown in FIG. 6, there is a significant amplitude gradient in the beam profile and the amplitude variation across the beam for smaller delay thicknesses. Based on the model results for nodular cast iron materials, as shown in FIG. 6, an acceptable range of thicknesses is about between 32 and 40 mm. As the Lucite thickness is increased the gradient of the amplitude falls and the slope almost becomes zero with thicknesses around 32 and 40 mm. For a Lucite delay thickness above 40 mm, an amplitude gradient is observed. An optimum Lucite delay thickness of around 35 mm is observed. Based on the modeling results shown in FIG. 6, a uniform sensitivity for defects across a 30-mm thick nodular iron piece is expected for a single-element probe that includes a 35-mm thick polycarbonate delay element. Simulation results on the variation of SNR as a function of frequency for a single-element probe with a polycarbonate delay element also showed substantially higher SNR compared to delay elements made of other materials, such as quartz.

As summarized hereinabove, simulation performance results of presently used single- and dual-element probes in nodular cast iron materials have shown that the performance of the novel and advantageous single-element probes disclosed are better as compared to the conventional dual-element probes. In one favored embodiment, a single-element probe optimized for higher performance uses a 35-mm-thick Lucite delay element material and an operating frequency of around 4 MHz. In this embodiment, the diameter of the Lucite delay element chosen is 25.4 mm (1 in) or above in-order to avoid any sidewall reflections.

Further use of numerical simulations and further experimental tests on casting calibration blocks of various cast materials also provide another embodiment of a single-element probe that includes a 5-MHz transducer with a 32-mm thick Rexolite delay element. This embodiment achieved a SNR>3 for a 0.5-mm flat-bottom hole in nodular cast iron and a 3-mm flat-bottom hole in flake cast iron. As shown and explained hereinabove, the delay element is capable of reducing substantially microstructure noises while keeping the signals from defects. As understood by those of ordinary art, one of the differences between Lucite and Rexolite is that Rexolite is a polycarbone with greater toughness and slightly higher sound speed than Lucite. In some embodiments of the subject matter disclosed, Rexolite is preferred as it will hold up better to scrapping over a rough cast surface.

Besides flat casting surfaces, there are many casting surfaces with curvatures both concave and convex, such as, for example, but not to be considered as limiting the subject matter disclosed herein throughout, bore surfaces, cylinder surfaces, diaphragm surfaces, to name just a few. Range of curvatures may be broad, varying approximately from about 100 mm to about 1000 mm diameter or larger. When ultrasonic probes for flat surface inspection are applied to curved surface inspection, both signal amplitude and signal to noise ratio from defects could be reduced because of less sufficient coupling of ultrasonic waves at the interface between delay and casting surface. Natural focusing or defocusing caused by surface curvatures could also impact signal amplitude and signal to noise ratio from defects in castings.

Figure 7A:
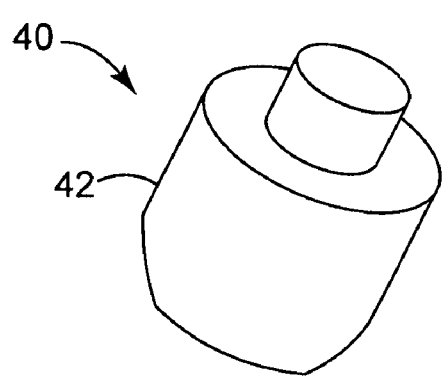
FIGS. 7A and 7B illustrate two views of a schematic of a single-element ultrasound inspection probe for curved surfaces according to an embodiment of the subject matter disclosed.
Figure 7B:
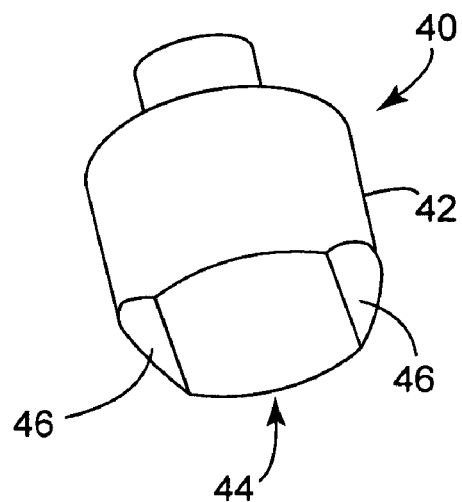

In order to better inspect curved surface castings FIGS. 7 (A and B) and 8 illustrate two exemplary embodiments of single-element ultrasound probes 40 and 50 configured to improve the ultrasonic energy coupling through the interface for a curved surface. FIGS. 7A and 7B show an example of a delay element 42 having a narrowed portion 44 configured to be disposed against a curved surface for inspection. The narrowed portion 44 is obtained by trimming portions 46 of the surface of the delay element 42 that is placed on the surface of the casting to be inspected. Diameters of the polycarbonate delay element 42 of FIGS. 7A and 7B range from about 6.4 mm (0.25 in) to about 51 mm (2 in). Delay heights for the single-element ultrasound probes 40 may range from about 5 mm to about 50 mm and delay bottom widths may range from 2.54 mm (0.1 in) to about 51 mm (2 in).

Figure 8:
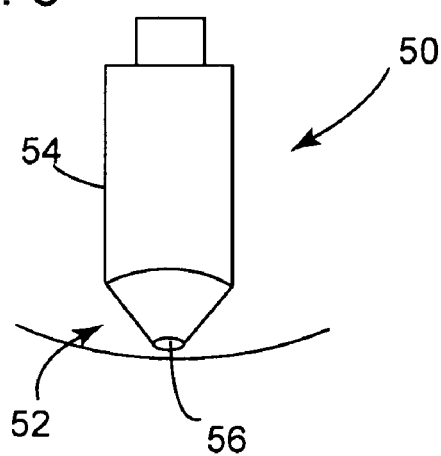
FIG. 8 illustrates a cross sectional view of a schematic of a single-element ultrasound inspection probe for curved surfaces according to an embodiment of the subject matter disclosed.

In the single-element ultrasound probe 50 illustrated in FIG. 8 the bottom end 52 of the polycarbonate delay 54 is machined with a spherical shape to slightly focus ultrasonic energy. In another embodiment, an end portion of the delay may be conical, as shown. The other end of the cone has a small opening 56, which is in contact with a curved surface of the casting during inspection. This design combines the filtering effect from a polycarbonate delay with slightly focused ultrasonic beam and narrow cone opening to achieve the optimal inspection results on castings having curved surface.

Methods of detecting a defect in a noisy material are also within the scope of the subject matter disclosed herein. Such methods include steps of emitting an amount of acoustic energy from an acoustic crystal element through a polycarbonate delay layer attached to the acoustic crystal element, a surface of the polycarbonate delay being in contact with a surface of the noisy material; and detecting the defect in the noisy material based on a measurement of a portion of the emitted acoustic energy scattered by the defect through the polycarbonate delay. In addition, such methods may also include steps of emitting the amount of acoustic energy from the acoustic crystal element through a polycarbonate delay layer selected from the group consisting of a Lucite delay layer and a Rexolite delay layer and the noisy material is selected from the group consisting of a composite material, a ceramic, a structurally porous material, a nodular cast iron, a flake cast iron, and a cast steel. When detecting defects in a nodular cast iron, these defects may have a characteristic dimension of about 0.5 mm or greater and be located at a depth of up to 40 mm from the surface of the nodular cast iron. When detecting defects in a flake cast iron, the defect may have a characteristic dimension of about 3.0 mm or greater and be located at a depth of up to 40 mm from the surface of the flake cast iron.

As already explained herein, the noted methods are also applicable to noisy materials having a curved where the surface of the polycarbonate delay layer in contact with the surface of the noisy material is narrower than a surface of the polycarbonate delay layer attached to the acoustic crystal element or where the polycarbonate delay layer is hollow and filled with a fluid and includes a conical piece having an opening disposed on an end portion of the hollow polycarbonate delay.

While the disclosed embodiments of the subject matter described herein have been shown in the drawings and fully described above with particularity and detail in connection with several exemplary embodiments, it will be apparent to those of ordinary skill in the art that many modifications, changes, and omissions are possible without materially departing from the novel teachings, the principles and concepts set forth herein, and advantages of the subject matter recited in the appended claims. Hence, the proper scope of the disclosed innovations should be determined only by the broadest interpretation of the appended claims so as to encompass all such modifications, changes, and omissions. In addition, the order or sequence of any process or method steps may be varied or re-sequenced according to alternative embodiments. Finally, in the claims, any means-plus-function clause is intended to cover the structures described herein as performing the recited function and not only structural equivalents, but also equivalent structures.

What is claimed is:

1. An ultrasound probe to inspect a defect in a noisy material, comprising:
   a polycarbonate delay layer having a first surface configured to be disposed on a surface of the noisy material; and
   at least one acoustic crystal element disposed on a second surface of the polycarbonate delay layer,
   wherein the surface of the noisy material is curved and an end portion of the polycarbonate delay layer having the first surface is narrower than a second end portion having the second surface.

2. The ultrasound probe according to claim 1, wherein the polycarbonate delay layer is selected from a group consisting of a Lucite delay layer and a Rexolite delay layer.

3. The ultrasound probe according to claim 1, wherein the polycarbonate delay layer is a Lucite delay layer having a height between 20 and 40 mm.

4. The ultrasound probe according to claim 3, wherein a driving frequency of the at least one acoustic crystal element ranges from about 1 MHz to about 5 MHz.

5. The ultrasound probe according to claim 3, wherein the polycarbonate delay layer is a Rexolite delay layer having a height between 20 and 40 mm.

6. The ultrasound probe according to claim 1, wherein a width of the Lucite delay layer is 25.4 mm or greater.

7. The ultrasound probe according to claim 1, wherein the noisy material is selected from the group consisting of a composite material, a ceramic, a structurally porous material, a nodular cast iron, a flake cast iron, and a cast steel.

8. The ultrasound probe according to claim 7, wherein the cast material is a nodular cast iron and the defect has a characteristic dimension of about 0.5 mm or greater.

9. The ultrasound probe according to claim 8, wherein the defect is a subsurface defect located at a depth of up to 40 mm from the surface of the nodular cast iron.

10. The ultrasound probe according to claim 7, wherein the cast material is a flake cast iron and the defect has a characteristic dimension of about 3.0 mm or greater.

11. The ultrasound probe according to claim 10, wherein the defect is a subsurface defect located at a depth of up to 40 mm from the surface of the flake cast iron.

12. The ultrasound probe according to claim 1, wherein the at least one acoustic crystal element is a dual element probe or an array probe.

13. The ultrasound probe according to claim 12, wherein the array probe is a one-dimensional array probe or a two-dimensional array probe.

14. An ultrasound probe to inspect a defect in a noisy material, comprising:
- a polycarbonate delay layer having a first surface configured to be disposed on a surface of the noisy material; and
- at least one acoustic crystal element disposed on a second surface of the polycarbonate delay layer, wherein the surface of the noisy material is curved and an end portion of the polycarbonate delay layer is conical having an opening, the opening of the conical end portion being configured to be disposed on the surface of the noisy material.

15. A single-element acoustic probe to inspect a defect in a noisy material, comprising:
- means for reducing sensitivity to background noise from a microstructure of the noisy material and for increasing sensitivity to a scatter acoustic signal from the defect, said means having a first surface configured to be disposed on a surface of the cast material; and
- an acoustic crystal element disposed on a second surface of the means for reducing sensitivity to background noise from a microstructure of the noisy material and for increasing sensitivity to an scatter acoustic signal from the defect, said acoustic crystal element being configured to generate an acoustic signal to be scattered by the defect.

16. A method of detecting a defect in a noisy material, the method comprising:
- emitting an amount of acoustic energy from an acoustic crystal element through a polycarbonate delay layer attached to the acoustic crystal element, a surface of the polycarbonated delay being in contact with a surface of the noisy material; and
- detecting the defect in the noisy material based on a measurement of a portion of the emitted acoustic energy scattered by the defect through the polycarbonate delay, wherein the surface of the noisy material is curved and the surface of the polycarbonate delay layer in contact with the surface of the noisy material is narrower than a surface of the polycarbonate delay layer attached to the acoustic crystal element.

17. The method according to claim 16, wherein the emitting further comprises emitting the amount of acoustic energy from the acoustic crystal element through a polycarbonate delay layer selected from the group consisting of a Lucite delay layer and a Rexolite delay layer and the noisy material is selected from the group consisting of a composite material, a ceramic, a structurally porous material, a nodular cast iron, a flake cast iron, and a cast steel.

18. The method according to claim 17, wherein the detecting further comprises detecting the defect in the nodular cast iron, the defect having a characteristic dimension of about 0.5 mm or greater and being located at a depth of up to 40 mm from the surface of the nodular cast iron.

19. The method according to claim 17, wherein the detecting further comprises detecting the defect in the flake cast iron, the defect having a characteristic dimension of about 3.0 mm or greater and being located at a depth of up to 40 mm from the surface of the flake cast iron.

20. A method of detecting a defect in a noisy material, the method comprising:
- emitting an amount of acoustic energy from an acoustic crystal element through a polycarbonate delay layer attached to the acoustic crystal element, a surface of the polycarbonated delay being in contact with a surface of the noisy material; and
- detecting the defect in the noisy material based on a measurement of a portion of the emitted acoustic energy scattered by the defect through the polycarbonate delay, wherein the surface of the noisy material is curved and the emitting further comprises emitting the amount of acoustic energy from the acoustic crystal element through a polycarbonate delay having a conical end portion having an opening therein, the opening of the conical piece being in contact with the surface of the noisy material.

21. An ultrasound probe to inspect a defect in a noisy material, comprising:
- a polycarbonate delay layer having a first surface configured to be disposed on a surface of the noisy material; and
- at least one acoustic crystal element disposed on a second surface of the polycarbonate delay layer,
- wherein the noisy material is selected from the group consisting of a composite material, a ceramic, a structurally porous material, a nodular cast iron, a flake cast iron, and a cast steel.

* * * * *